Figure 1:
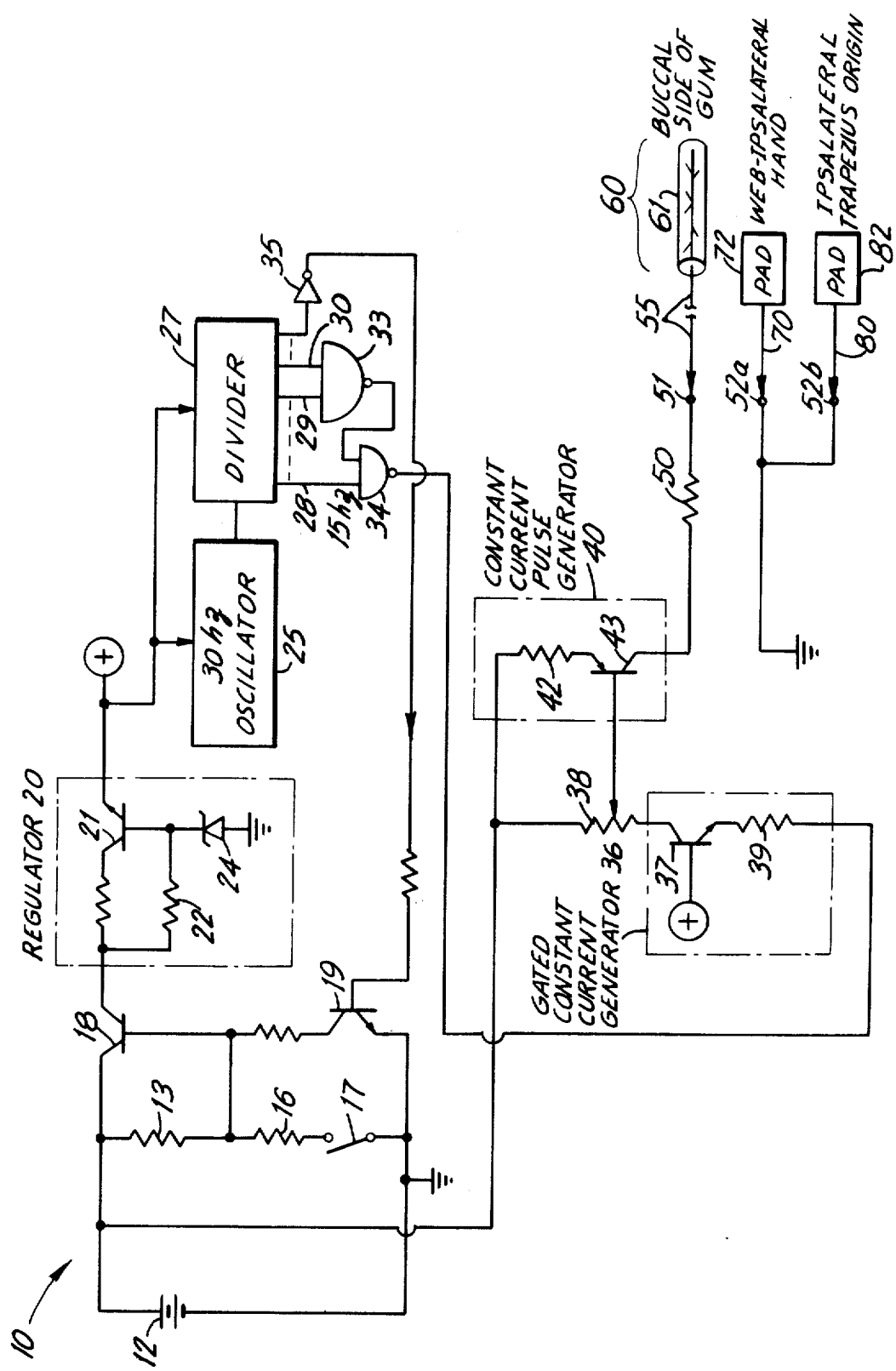

United States Patent [19]

Liss et al.

[11] Patent Number: 4,550,733

[45] Date of Patent: Nov. 5, 1985

[54] ELECTRONIC DENTAL ANALGESIA APPARATUS AND METHODOLOGY

[75] Inventors: Saul Liss; Bernard S. Liss, both of Glen Rock, N.J.

[73] Assignee: Pain Suppression Labs, Inc., Elmwood Park, N.J.

[21] Appl. No.: 569,476

[22] Filed: Jan. 9, 1984

[51] Int. Cl.[4] .............................................. A61N 1/34
[52] U.S. Cl. ................................... 128/421; 128/419 R
[58] Field of Search ..................... 128/419 R, 421–423, 128/787

[56] References Cited

U.S. PATENT DOCUMENTS

| 535,905 | 3/1895 | Horton, Jr. et al. | 128/787 |
| 2,004,751 | 6/1935 | Fischer et al. | 128/423 R |
| 3,640,284 | 2/1972 | De Langis | 128/422 |
| 3,791,373 | 2/1974 | Winkler et al. | 128/422 |
| 3,902,502 | 9/1975 | Liss et al. | 128/422 |
| 4,071,033 | 1/1978 | Nawracaj et al. | 128/422 |
| 4,109,660 | 8/1978 | Nesmeyanov et al. | 128/419 R |
| 4,155,366 | 5/1979 | DiMucci | 128/421 |

FOREIGN PATENT DOCUMENTS

| 2339648 | 2/1975 | Fed. Rep. of Germany | 128/419 R |
| 2500309 | 8/1982 | France | 128/422 |
| WO79/01082 | 12/1979 | PCT Int'l Appl. | 128/419 R |
| 0605603 | 5/1978 | U.S.S.R. | 128/421 |

OTHER PUBLICATIONS

Dubner, "Neurophysiology of Pain", *Dent. Clin. North Am.*, 1978, 22:11–30.
Price et al., "Neurons that Subserve the Sensory Discriminative Aspects of Pain", *Pain*, 1977, 3:307–338.
Kerr, "Pain: A Central Inhibitory Balance Theory", *Mayo Clin. Proc.*, 1975, 50:685–690.
Melzack et al., "Pain Mechanisms: A New Theory", *Science*, 1965, 150:971–979.

*Primary Examiner*—William E. Kamm
*Assistant Examiner*—Mitchell J. Shein
*Attorney, Agent, or Firm*—Stephen B. Judlowe

[57] ABSTRACT

Dental electronic analgesia apparatus and methodology employs a transcutaneous electronic wave to suppress perceived pain during trauma associated with dental procedures. A first electrode is placed on the buccal side of the gum adjacent the work area, and second electrodes are disposed on the web of the ipsalateral hand and on the ipsalateral trapezius origin. An electronic current wave comprising relatively high frequency pulses with a low frequency amplitude modulation is then applied between the first to the second electrodes.

The apparatus of the instant invention has been found to block pain in most subjects with a low level current without any chemical intervention—or with a reduced dosage of local anesthesia.

3 Claims, 5 Drawing Figures

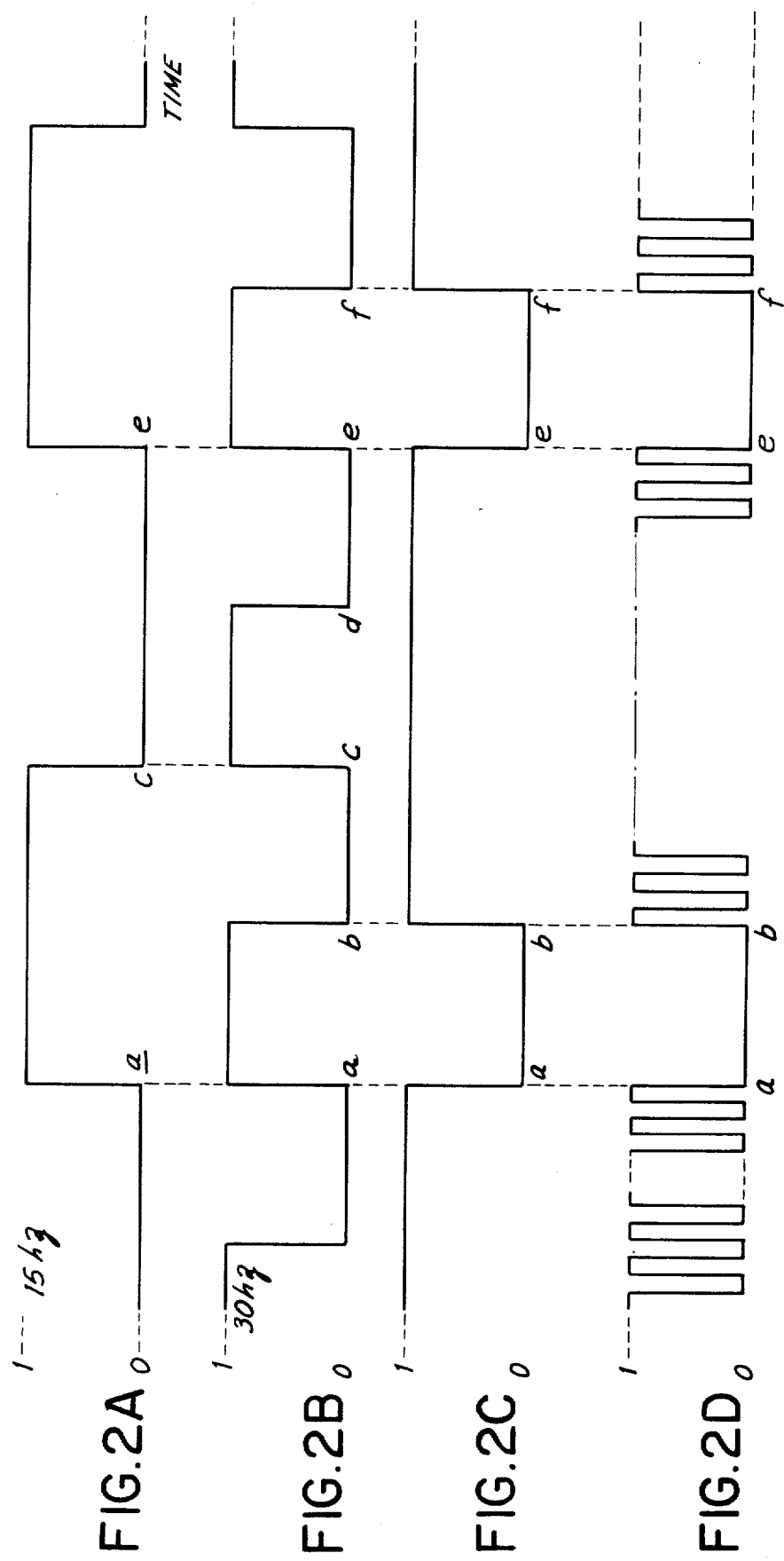

ELECTRONIC DENTAL ANALGESIA APPARATUS AND METHODOLOGY

DISCLOSURE OF THE INVENTION

This invention relates to electronic pain suppression apparatus and methodology and, more specifically, to dental analgesia apparatus and procedure for relieving pain during dental procedures.

It is an object of the present invention to provide improved dental analgesic apparatus and methodology.

More specifically, an object of the present invention is the electronic provision of dental analgesia in a safe, efficient and rapid manner to suppress perceived pain during dental procedures.

It is a further object of the present invention to provide electronic dental transcutaneous electronic nerve stimulating equipment operative at very low, milliampere current levels, which relieves perceived pain during dental procedure; and which for the most part is effective without requirement for chemical local anesthesia.

The above and other objects and features of the instant invention are realized in a specific illustrative dental electronic analgesia apparatus and methodology which employs a transcutaneous electronic wave to suppress perceived pain during trauma associated with dental procedures. A first electrode is placed on the buccal (cheek) side of the gum adjacent the work area, and second electrodes are disposed on the web of the ipsalateral (opposite) hand and on the ipsalateral trapezius origin below the mastoid. An electronic current wave comprising relatively high frequency pulses with a low frequency modulation is then applied from the first to the second electrodes.

The apparatus of the instant invention has been found to block pain in most subjects with a relatively low level current without chemical intervention - or with a reduced dosage of local anesthesia.

The above and other features and advantages of the instant invention will become more clear from the following detailed description of a specific illustrative embodiment thereof, presented hereinbelow in conjunction with the accompanying drawing, in which:

FIG. 1 is a schematic diagram of electronic dental anesthesia apparatus embodying the principles of the present invention; and FIGS. 2A through 2D are wave forms illustrating the operation of the FIG. 1 apparatus.

To illustrate performance of the instant invention in overview, the apparatus of FIG. 1 is utilized to block pain perceived by a patient who is subjected to a trauma producing (e.g., invasive) dental procedure. A first electrode 60 (FIG. 1) is placed on the buccal side of the patient's gum adjacent the tooth or teeth subjected to the procedure. Additional electrodes 72 and 82 are respectively placed on the web of the ipsalateral hand, i.e., the hand on the side of the body opposite to the tooth or teeth being worked upon, and on the ipsalateral trapezius origin. An electronic wave (depicted in FIG. 2D) is then applied between the first electrode 60, and the electrodes 72 and 82 which are connected on common. The wave form of FIG. 2D comprises a low level (less than 4 milliamperes) pulse train of relatively high frequency, e.g., between 12 and 20 khz modulated in amplitude by a relatively low frequency wave in the range of 8 to 20 hz. The low frequency wave is preferably non-symmetrical (that shown in FIG. 2D), for example, characterized by a 3:1 duty cycle, being on three quarters of the time and off one quarter of the recurring period. For concreteness only and without limitation, it will hereinafter be assumed that the high frequency pulse occurs at a 15 khz rate and 1-1.5 m.a. level, while being subject to a 15 hz modulation with a 3:1 duty factor.

I have found that the wave of FIG. 2D is effective in the majority of patients to block the pain perceived during dental procedures. In a fraction of that minority requiring additional chemical intervention, the local anesthesia required is reduced.

The particular mechanism causing elimination of the perceived dental pain is believed to follow from the increase in serotonin produced by the body responsive to the low frequency modulation envelope introduced into the body, with the high frequency wave constituent serving as a transcuatneous carrier for the low frequency modulation.

Various theories have been proposed to characterize the mechanism of perceived pain, and of the manner in which such pain is obviated. The following are presented for possible edification, and without limitation, as to the instant invention. Beginning with a discussion of a purely anatomical explanation, the autonomic nervous system is governed by two anatagonistic systems: the sympathetic and the parasympathetic. The first is mediated by nerves which release norepinephrine and the second by those which release serotonin. The neurotransmitter serotonin is thought to be associated with behavioral sedation and sleep, increased para-sympathetic output in the periphery, decreased locomotor activity and reduced responsiveness to external stimulation. An increase in brain serotonergic neurotransmission can lead to the reversal of biological arousal, and therefore suppression of the sensation of pain. The disclosure of Rita B. Messing, "Behavioral Effects of Serotonin Neurotoxins" *Annals, N.Y. Acad. Sci.,* 1978:480–496, is hereby incorporated by reference. Electronic stimulation of tissue has been shown to increase the brain serotonergic neurotransmission and thus produce analgesia.

Another explanation of the analgesic effects of the presently claimed invention depends on the interference with the neural signal's path. The first-order neuron in the pathway for pain and temperature synapses as it enters the spinal cord with a neuron in the dorsal column of gray matter. The axon of this second-order neuron crosses the gray matter to the opposite side of the spinal cord, where it courses upward as a component of the lateral spinothalamic tract. Passing to the thalamus the fiber synapses in a nucleus in this region with a third-order neuron, which relays the impulse to the sensory area of the cerebral cortex. Upon arrival of the impulse to the fifth cranial nerve, pain from the face and head is consciously perceived.

The use of electroanalgesia to block pain may be explained by the "spinal gating" hypothesis. Stimulation of afferent inhibitory neurons, would "close the spinal gate" to prevent pain impulses from being propagated from the spinal cord to the brain. The gate mechanism may be embedded in the cells of the substantia gelatinosa. The mechanism would both sum up the net stimulus due to excitatory and inhibitory signals converging on the spinal cord from afferent fibers, and then transmit the net signal to brain centers. (There may be a second gate, blocking signals that bypass the first gate, higher up in the central nervous system, either in the brainstem or the central medianum of the Thalamus.) Second, it would coordinate both pain and its interpretation so that either the pain impulses themselves would not reach the brain centers, or the coordination brought about by the gating system would alter the interpretation and pain would not be perceived.

A third theory of pain suppression depends on the nociceptive system, defined as an ancestral multi integrated apparatus which includes pain sensation. Pain is produced by excitation of functionally distinct types of nociceptors which have yet to be entirely defined anatomically. According to Becker, "The Basic Biological Data Transmission and Control System Influenced by Electrical Forces" *Annals N.Y. Acad. of Sci.*, 1972, 236–239, our sophisticated action potential system coexists with this basic primitive analog system. Different types of pain may be related to the activation of different proportions of both systems. According to Melzack and Wall, "Pain Mechanisms, a New Theory" *Science* 1965, 150: 971–979, large non-nociceptive fibers exert presynaptic inhibitory effects on the endings of small nociceptive fibers in the dorsal horn. Substantia gelatinosa interneurons mediate this inhibition. The larger fiber discharge tends to block the transmission of input from the small afferent neurons before it reaches the relay neurons. According to their "gate control theory," electrical currents achieve a quantitative superiority to nociceptive impulse at the "neurologic gates" that transmit pain to higher centers; thus transmission of painful impulses is blocked. Further, Kerr in "Pain," *Mayo Clin Proc.*, 1975, 50: 685–590, notes that electronic stimulation of large fiber input alleviates pain because of its affect on the central nociceptive pathways. When large fibers are electrically excited, widespread activation of gelatinosa neurons results in inhibitory impulses being delivered to marginal neurons.

Other theories of electroanalgesia include the inducement of neurons to manufacture an endogenous opiate that interacts with pain receptors to produce analgesia similar to that produced by morphine, *See.* Meyer CA, Fields HL: "Causalgia treated by selective large fibre stimulation of peripheral nerve," *Brain* 1972; 95: 163–168; and the effect on trigeminothalamic A - beta neurons, *See* Dubner R: "Neuro physiology of Pain." *Dent Clin North Am* 1978; 22: 11–30.

While the precise operative mechanism may be the subject of debate, the fact of the dental analgesia produced by the instant invention is not.

As above noted, the composite electrode 60 is inserted in the oral cavity on the buccal side of the gum in the work area vicinity. The electrode is connected via a lead 55 to a connector terminal 51 associated with the electronic apparatus, where the lead terminates in a wire broach area 62 having plural barbs projecting radially outward and canted therefrom. The barbed wire broach 62 is inserted into a cotton swab 61 which is made wet to provide electrical conductivity between the patient's gum and the wire end 62. The barbed projections on wire broach 62 reduce the impedance between the wetted cotton and the metallic conductor 62 by increasing contact surface are while also mechanically retaining the cotton. The electrodes 72 and 82 constitute connection lands or pads to the patient's skin in any of the diverse means per se well known to those skilled in the art.

The FIG. 1 electronic apparatus 10 for generating and applying the wave form of FIG. 2D will now be specifically considered. A battery 12 is connected to a PNP series pass transistor 18 which, in turn, selectively passes the voltage from battery 12 through a voltage regulator 20 to form the positive direct current voltage supply for the apparatus 10 electronics. The unit is first turned on by momentarily closing a power-on switch 17. This applies a low voltage to the base of PNP transistor 18, turning that device on and effectively coupling the potential of battery 12 to a series pass transistor 21 in the voltage regulator 20. Because the final output of a counter or divider chain 27 is initially low on power turn on, the resulting high output of inverter 35 applies a high potential to the base of transistor 19, turning it on and thereby latching PNP transistor 18 to its conductive condition when switch 17 is released. This maintains the electronic apparatus on for a desired period (in excess of the time required to complete the dental procedure) which is determined by the frequency of an oscillator 25 and the division factor of the divider 27, i.e., the period required for the most significant stage of the counter 27 to reach its high or binary "1" state. The switched power supply assures that the electronic apparatus is not inadvertently left on to unduly discharge the battery 12.

The regulated output of battery 12 applied through PNP transistor 18 is converted to a lower regulated value by the regulator 20. Regulator 20 is per se well known and includes the series pass NPN transistor 21 having a constant voltage applied to the base thereof by a Zener diode 24 energized by a resistor 22. The constant potential output of regulator 20, which serves as the supply voltage for much of the remaining electronics of FIG. 1, is the characteristic reverse excitation voltage of Zenor diode 24 less about 7/10 of a volt for the base-emitter drop of transistor 21.

As above noted, the active power supply interval for circuit 10 of the drawing is fixed and preset to a period which will exceed normal dental procedures. The above-discussed time out circuitry is employed to assure that the unit is not inadvertently left on. Many ways of achieving this result will be readily apparent to those skilled in the art. For example, a variable time out may be provided by employing a switch to connect the input of inverter 35 to varying ones of the more significant stage outputs of the pulse counter chain 27. Yet further, separate electronic or electromechanical timer apparatus, fixed or variable, all per se well known, may be employed to supply a positive potential to the base of transistor 19 for the desired "on" period; and to switch off the base drive to transistor 19, thereby turning off series pass transistor 18, when the desired operative period has passed.

A time base oscillator 25 supplies an input to the pulse counter or divider chain 27. The frequency of oscillator 25 is chosen for convenience to be an integral multiple of the pulse frequency (FIG. 2D) desired for delivery to the patient. For the assumed 15 khz desired frequency, a 30 khz oscillation repetition rate may be usefully employed for oscillator 25, such that the 15 khz signal is derived at a divide-by-two tap 28 of divider chain 27. The 15 khz signal is supplied as one input to a NAND gate 34, the output of which corresponds to the ultimately desired wave of FIG. 2D. Outputs 29 and 30 of divider 27 are supplied as inputs to a NAND gate 33, the output of which is supplied as a second input to the NAND gate 34. The output 29 of divider 27 supplies the 30 hz wave of FIG. 2B (pulse division factor 1,000 at tap 29), while the 15 hz wave of FIG. 2A is supplied at a divider output 30 (divider factor: 2,000). Logic gate 33 generates the output wave of FIG. 2C, being at its high or Boolean "1" value when either of the waves of FIGS. 2A or 2B is low (i.e., preceding the time a, during the interval b-e, - and following time f). Correspondingly, during the periods a-b and e-f when the output at divider 27 taps 29 and 30 are both high, the output of gate 33 is low (Boolean "0" value).

The wave form of FIG. 2C is supplied as one input to the gate 34 together with the 15 khz pulse train at the divide-by-two counter 27 output port 28. Accordingly, the output of NAND gate 34 switches between its high and low state during the periods when the FIG. 2C wave is high, i.e., preceding time a, during the interval b-e, following the time f, and so forth for the recurring pattern illustrated by FIGS. 2A-2D.

The voltage wave form of FIG. 2D is converted to a current in the milliampere range for application to the patient by the following circuitry of FIG. 1. As a first matter, a gated constant current generator 36 passes a gated current (either off or of a fixed value) through a potentiometer 38 under control of the output of the NAND gate 34. When the output of NAND gate is low, a transistor 37 in constant current generator 36 is on and a current substantially given by the positive potential output of regulator 20 (applied to the base of transistor 37) less a 7/10 of a volt base emitter drop for the transistor 37, divided by the resistance value of the resistance 39 in the emitter circuit of transistor 37. The voltage at the variable tap of the potentiometer 38 is supplied to the base of a PNP transistor 43 of a constant current pulse generator 40. The output of pulse generator 40 is a current which switches between its off (zero current) state, and a value given by the voltage at the potentiometer 38 tap, less a diode drop for the emitter-base of transistor 43, divided by the resistance value of resistor 42 connected in the emitter circuit of the PNP device 43. This pulsed current output of pulse generator 40 corresponds in wave form to FIG. 2D, and is at a level, determined by the setting of potentiometer 38, in the low milliampere range. It is this current pulse which is ultimately delivered to the patient to provide the requisite dental analgesia.

In a typical application the patient is provided with the potentiometer 38. The potentiometer is first turned up so that the administered current pulses provide a noticeable tingling sensation in the oral cavity of the patient. The patient is then instructed to turn down the potentiometer adjustment until the sensation just disappears. This will provide the amount of transcutaneous electronic stimulation to suppress the perception of pain otherwise engendered by the dental procedure underway. The potentiometer setting may be adjusted by the patient as required as the dental work progresses.

The current pulses from generator 40 pass through a protective, series limiting resistor 50 to an output terminal 51. It there flows via the lead 55 connected to terminal 51 to the barbed wire broach 62 and reaches the patient's gum through the wetted cotton 61 surrounding lead 62 disposed on the buccal side of the patient's gum at the work site. The current transcutaneously passes into the patient at the buccal gum station, flows through the patient, and returns to electronic ground via the electrode pads 72 and 82, respectively disposed on the web of the patient's ipsalateral hand and on the ipsalateral trapezius origin, respectively. Electrodes 72 and 82 are connected to electronic system ground via leads 70 and 80, and apparatus terminal ports 52a and 52b.

As above noted, the apparatus and methodology of the instant invention, usually per se but sometimes with the administration of supplementary chemical anesthesia, blocks the perception of pain which would otherwise occur by involvement with the fifth cranial or trigeminal nerve system. The apparatus and methodology has manifest advantages for both the dentist and the patient, avoiding the pain, discomfort and delay associated with otherwise required injected chemical anesthesia.

The above described arrangement and methodology are merely illustrative of the principles of the present invention. Numerous modifications and adaptations thereof will be readily apparent to those skilled in the art without departing from the spirit and scope of the present invention.

What is claimed is:

1. A method for suppressing pain otherwise associated with a dental procedure in a subject's oral cavity including the steps of securing a first electrode at the buccal side of the gum of a subject adjacent the work area, securing second ad third electrodes connected electrically in common to the web of the subject's ipsalateral hand and to the subject's ipsalateral trapezius origin, and supplying an electrical wave comprising a high frequency amplitude modulation to said first, and said second and third electrodes.

2. The method as in claim 1, wherein the frequency of said high frequency electrical wave was in the range 12-20 khz, wherein said low frequency modulation is in the range 8-20 hz, and wherein said wave does not exceed about 4 milliamperes.

3. The method as in claim 11 or 12, wherein said amplitude modulation is non-symmetrical.

* * * * *

UNITED STATES PATENT AND TRADEMARK OFFICE
CERTIFICATE OF CORRECTION

PATENT NO. : 4,550,733
DATED : November 5, 1985
INVENTOR(S) : Saul Liss, et al.

It is certified that error appears in the above—identified patent and that said Letters Patent is hereby corrected as shown below:

Column 6, line 39, change "ad" to -- and --;

Column 6, line 50, change "claim 11 or 12" to

-- claim 1 or 2 --.

Signed and Sealed this

Eleventh Day of February 1986

[SEAL]

Attest:

DONALD J. QUIGG

Attesting Officer    Commissioner of Patents and Trademarks